United States Patent [19]

Blechner

[11] 4,412,822
[45] Nov. 1, 1983

[54] DENTAL ARTICULATOR WITH REMOVABLE TRAY

[76] Inventor: Charles Blechner, 8 Lighthouse Road, Great Neck, N.Y. 11024

[21] Appl. No.: 372,275

[22] Filed: Apr. 27, 1982

Related U.S. Application Data

[63] Continuation of Ser. No. 201,821, Oct. 29, 1980, abandoned.

[51] Int. Cl.³ ............................................ A61C 11/00
[52] U.S. Cl. ...................................... 433/60; 433/54; 433/57; 433/59
[58] Field of Search ...................... 433/60, 54, 57, 59, 433/65

[56] References Cited

U.S. PATENT DOCUMENTS

| | | | |
|---|---|---|---|
| 321,457 | 7/1885 | Smith | 433/65 |
| 537,812 | 4/1895 | Bragg | 433/60 |
| 824,096 | 6/1906 | Crate | 433/65 |
| 1,096,195 | 5/1914 | Roberts | 433/60 |
| 1,271,161 | 7/1918 | Hall | 433/60 |
| 1,319,737 | 10/1919 | Wadsworth | 433/59 |
| 2,348,606 | 5/1944 | Cayo | 433/63 |
| 2,617,195 | 11/1952 | Perkell et al. | 433/65 |
| 2,824,371 | 2/1958 | Granger | 433/57 |
| 2,911,722 | 11/1959 | Benfield et al. | 433/60 |
| 3,123,914 | 3/1964 | De Pietro | 433/60 |
| 3,465,443 | 9/1969 | Schwartz et al. | 433/60 |
| 3,808,689 | 5/1974 | Spinella | 433/60 |
| 4,189,837 | 2/1980 | Stele | 433/60 |
| 4,207,677 | 6/1980 | Lampert | 433/60 |

FOREIGN PATENT DOCUMENTS

| | | | |
|---|---|---|---|
| 960846 | 4/1950 | France | 433/60 |
| 2024018 | 1/1980 | United Kingdom | 433/60 |
| 2035091 | 6/1980 | United Kingdom | 433/60 |

*Primary Examiner*—John J. Wilson
*Attorney, Agent, or Firm*—Morgan, Finnegan, Pine, Foley & Lee

[57] ABSTRACT

A dental articulator has a tooth supporting tray secured to a platform by a key and keyway wherein the sidewalls of the keyway are resiliently supported to permit yielding of the sidewalls to overcome any clogging by particulate matter which may be present in a place of use of the articulator. A set of legs upstanding from the tray maintains orientation of the tray relative to the platform.

14 Claims, 13 Drawing Figures

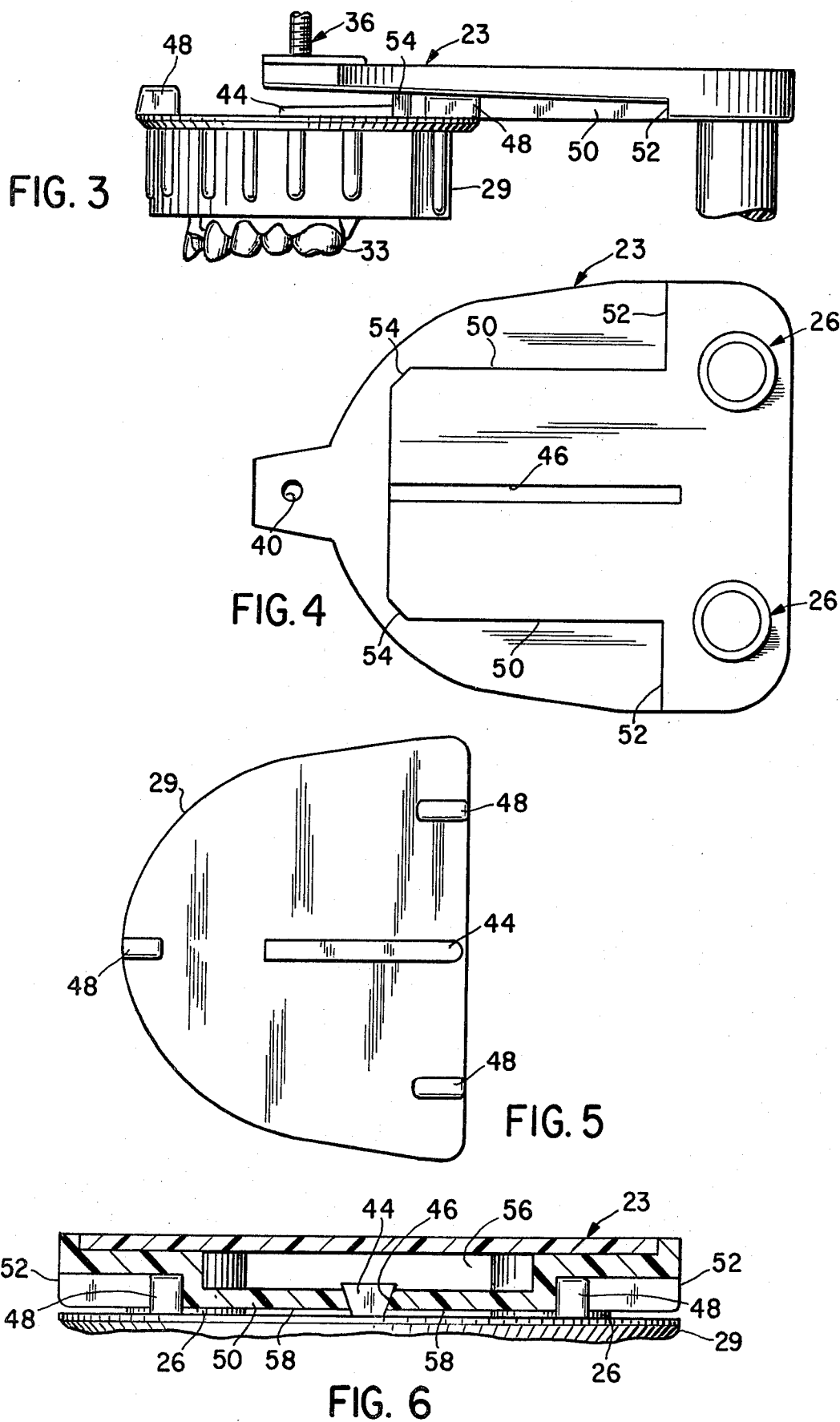

DENTAL ARTICULATOR WITH REMOVABLE TRAY

This is a continuation, of application Ser. No. 201,821 filed Oct. 29, 1980, now abandoned.

BACKGROUND OF THE INVENTION

This invention relates to dental articulators and, more particularly, to the connection of a tooth supporting tray by a keyway to the articulator frame.

Articulators are used for supporting and orienting a cast of the dental arch during the fabrication of prosthetic devices. The tooth supporting trays have been rigidly secured to platforms of the articulator frame by plaster, the plaster forming a permanent bond which is retained throughout the fabrication process. The foregoing form of articulator suffers a disadvantage in that the dental technician cannot separate the casting or model of the dental arch from the articulator, but must perform all steps of the fabrication while the casting is attached to the articulator.

A problem arises in the event that an attempt be made to detachably secure the tooth supporting trays to the articulator frame. First, it is noted that the articulators are used in laboratories wherein various powders such as plasters and other substances are present which may come in contact with the tray or the frame and, thereby, jam a mechanism which might be used for detachably securing the trays to the frame. An additional problem attendant the connection of the trays to the frame is the need for retaining the orientation of the trays relative to the articulator.

SUMMARY OF THE INVENTION

The aforementioned problems are overcome and other advantages are provided by an articulator wherein the trays are secured to upper and lower platforms of the articulator frame by keys and keyways. In accordance with the invention, the keys fit loosely in the keyways and extend only a portion of the length of the keyways. Preferably, the keys and the keyways are made of semi-rigid material, such as a soft plastic, to permit distension of the material to clear a blockage which may be formed by particulate matter found in a laboratory environment.

A set of noncolinear legs are slidably mounted between a tray and a platform of the articulator for entering into contact therebetween subsequent to the entry of the key into the keyway. The legs provide for the orienting of the tray relative to the platform.

In a preferred embodiment of the invention, the keyway is located on the platform, while the key and the set of the legs are located on the tray. Thereby, a tray carrying a casting is readily secured to the platform by inserting the key into the keyway and then advancing the key along the keyway to bring the legs in contact with the platform. As the legs contact the platform, the key is tightened against the keyway. Clearance between the key and the keyway, as well as between the legs and the platform, permit the securing and releasing of the tray relative to the platform even in the presence of particulate matter at the interface between the tray and the platform.

BRIEF DESCRIPTION OF THE DRAWINGS

The foregoing features and other aspects of the invention are explained in the following description taken in connection with the accompanying drawings wherein:

FIG. 3 is a side elevation view of the upper platform of the articulator of FIG. 2 with a tray thereof being shown partially inserted into the platform;

FIG. 4 is a plan view of the upper platform taken along the line 4—4 in FIG. 1;

FIG. 5 is a plan view of the tray taken along the line 5—5 of FIG. 1;

FIG. 6 is a sectional view of the interface between the platform and the tray taken along the line 6—6 in FIG. 2;

DESCRIPTION OF THE PREFERRED EMBODIMENT

Figure 1:
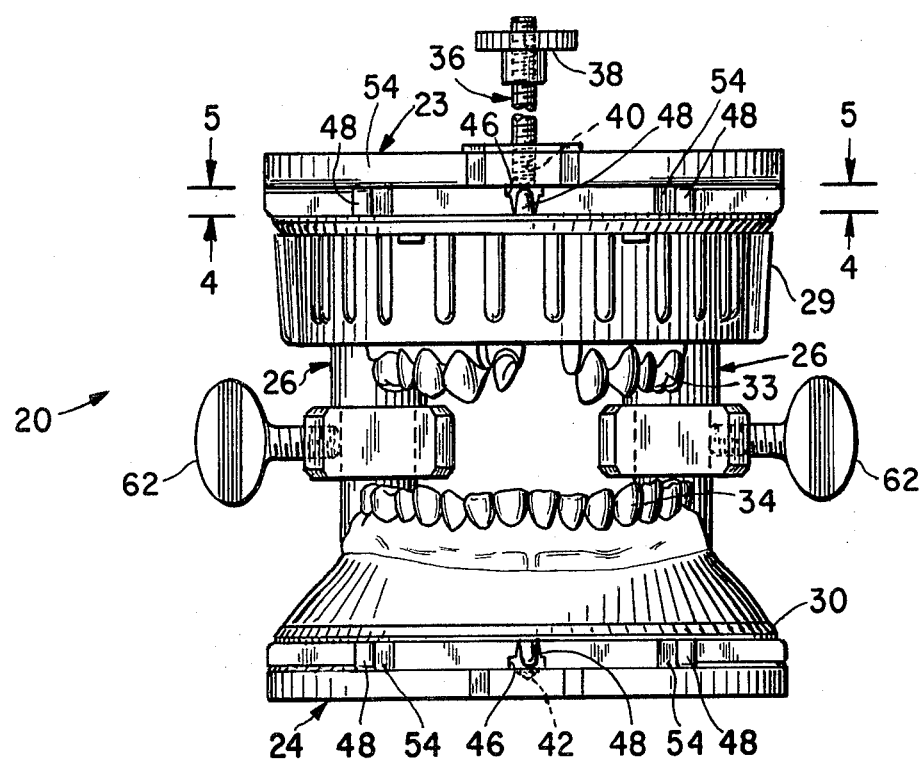
FIGS. 1 and 2 are, respectively, front and side elevation views of an articulator constructed in accordance with the invention, a spacer screw being shown in a stowed position in FIG. 1 and in a deployed position in FIG. 2.
Figure 2:
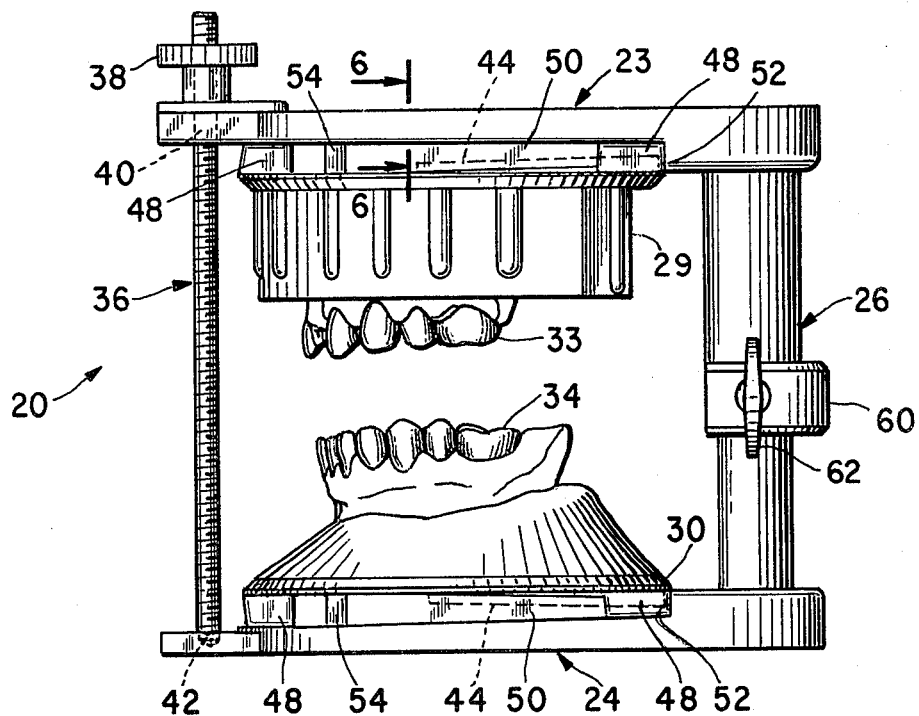

Referring now to the FIGS. 1-3, a dental articulator 20, constructed in accordance with the invention, comprises upper and lower platforms 23-24 joined together by telescoping legs 26. Upper and lower trays 29-30, respectively, support dental castings 33-34 and are secured to the upper and lower platforms 23-24. The securing of castings to trays, and suitable materials for the fabrication of trays are taught in U.S. Pat. No. 3,808,689 which issued in the name of Spinella on May 7, 1974. The trays 29-30 incorporate two exemplary configurations of such trays which are useful for supporting dental castings in an articulator. The articulator 20 is also fabricated of a plastic material, such as those listed in the aforementioned Spinella patent, a semi-rigid plastic material such as nylon being preferred since such material can yield during the joining of a tray to a platform as will be described hereinafter.

The spacing between the upper and lower platforms 23-24 is readily adjusted by means of telescoping legs 26. A selected spacing between the upper and lower platforms 23-24 is maintained by means of friction between the upper and lower portions of the telescoping legs 26, and by means of a spacer 36 in the form of a threaded rod having a knurled nut 38 for locking the spacer 36 in position. The spacer 36 is threaded through a tapped hole 40 in a wing portion of the upper platform 23, the lower end of the spacer 36 pressing against a recess 42 in an anvil portion of the lower platform 24. For removal of the upper tray 29, the spacer 36 is raised to a stowed position as shown in FIG. 1. The spacer 36 may be fabricated of a metal, in which case a metallic insert (not shown) is advantageously secured within the hole 40.

In accordance with the invention, each of the trays 29-30 are detachably secured in the same manner to their respective platforms 23-24 by means of a key 44 and keyway 46. Each of the trays 29-30 is provided with a set of three legs 48 for orienting the trays 29-30 and for retaining their respective orientations. With respect to the upper platform 23 and its tray 29, the key 44 is formed integrally with the tray 29, and the keyway 46 is formed integrally with the platform 23. The key 44 is inclined by a small angle, on the order of one degree relative to tray 29 and, similarly, the keyway 46 is inclined at a corresponding angle relative to platform 23. Thereupon, upon attachment of the tray 29 into its platform 23 the key 44 advances along the keyway 46 and draws the tray 29 closer to the platform 23. The legs 48 are pressed against the platform 23 as the key 44 advances along its keyway 46. The legs 48 are spaced apart with two of the legs 48 being towards the rear of the tray 29 while a third one of the legs 48 is located at the front of the tray 29 to provide a three point positioning of the tray 29 relative to its platform 23. The foregoing description of the key 44, keyway 46 and legs 48 with respect to the tray 29 and platform 23 applies also with respect to the tray 30 and platform 24.

Referring also to FIGS. 4-6, the platforms 23-24 each include a guide 50, the outer edges of the guide 50 guiding the rear legs 48 of the trays 29-30, respectively, the aforementioned keyway 46 being located along a central line of the guide 50 for engagement with the key 44 as the rear legs 48 slide along the outer edges of the guide 50. While FIG. 4 shows only the upper platform 23 and its guide 50, by way of example, it is to be understood that the same structural configuration applies to the positioning of the guide 50 on the lower platform 24. At the rear of each guide 50 is a pair of heels 52 which serve as stops to the movement of the legs 48 during the insertion of the trays 29-30, respectively, into the platforms 23-24. The front corners 54 of the guides 50 are rounded to facilitate engagement of the rear legs 48 of the trays 29-30 with the guides 50 of the respective platforms 23-24. Also, it is to be understood that the configuration of the three legs 48 and the key 44 shown in FIG. 5 with respect to the upper tray 29 is employed in the construction of the lower tray 30.

As shown in FIG. 6, the key 44 has a vee-shaped cross section providing diverging side-walls which mate with correspondingly angled side-walls of the keyway 46. The side walls of the keyway 46 are undercut to produce a chamber 56 bounded by a pair of tongues 58 which resiliently support the side-walls of the keyways 46. While FIG. 6 shows the configuration of the keyway structure of the upper platform 23, by way of example, it is to be understood that the same keyway structure is employed in the lower platform 24.

In operation, therefore, the castings 33-34 are secured by conventional techniques to the trays 29-30 respectively. The trays 29-30 may be repetitively inserted and removed, respectively, from the platforms 23-24, the platforms 23-24 being adjustably spaced relative to each other by the telescoping legs 26 and the spacer 36.

The articulator 20 is commonly utilized in a laboratory for the fabrication of dental prosthetic devices. In the laboratory, materials such as plaster, metals and adhesives are commonly utilized. Particulate matter such as plaster particles may be present in the laboratory and, as the articulator 20 is manipulated by dental technician, such particulate matter may come in contact with the articulate 20. The foregoing structural features of the guide 50, the keyway 46, the key 44 and the legs 48 permits the repetitive insertion and removal of the trays 29-30 relative to the platforms 23-24 even when the mating surfaces of the trays and the platforms become coated with the foregoing particulate matter. The configuration of the legs 48 is such that particulate matter would be pushed aside from the pathway of the legs 48. Also, the region of contact between the legs 48 and either of the platforms 23-24 is sufficiently small so as to prevent the development of frictional forces associated with any possible accummulation of the particulate matter at the interface between surfaces of the legs 48 and either of the platforms 23-24. While the orientations of the key 44 and the keyway 46 of a tray 29 or 30 and its corresponding platform 23 or 24 are inclined, or angled, so as to draw the tray closer to the platform upon advancement of the key 44 along its keyway 46, the resiliency of the semi-rigid tongues 58 permit sufficient vertical displacement between the tray and platform for the clearance of the legs 48 about any accumulated particulate matter. Also, as shown in FIG. 6, the top of a key 44 is spaced apart from the bottom of its keyway 46 to insure adequate clearance even in the presence of the particulate matter. Thereby, the articulator 20 is rended immune to clogging by particulate matter as well as by such other materials as may be found in the laboratory.

Returning to FIG. 1, a clamp 60 with a thumb screw 62 therein is placed about the lower portion of each leg 26 to further stabilize the orientation of the upper platform 23 relative to the lower platform 24. The clamp 60 is set at a desired height whereupon the thumb screw 62 is tightened to secure the clamp 60 at the desired height. The upper portion of a leg 26 then rests upon the clamp 60. By use of the clamps 60 on the pair of legs 26, in combination with the spacer 36, there is provided a stable three-point positioning of the upper platform 23 relative to the lower platform 24. While the articulator 20 may be utilized without the clamps 60, the positioning relying solely on the support of the spacer 36 and on friction between the upper and lower portions of the legs 26, the use of the clamps 60 is preferred because of the greater positional accuracy.

ALTERNATIVE EMBODIMENTS OF THE INVENTION

Figure 7:
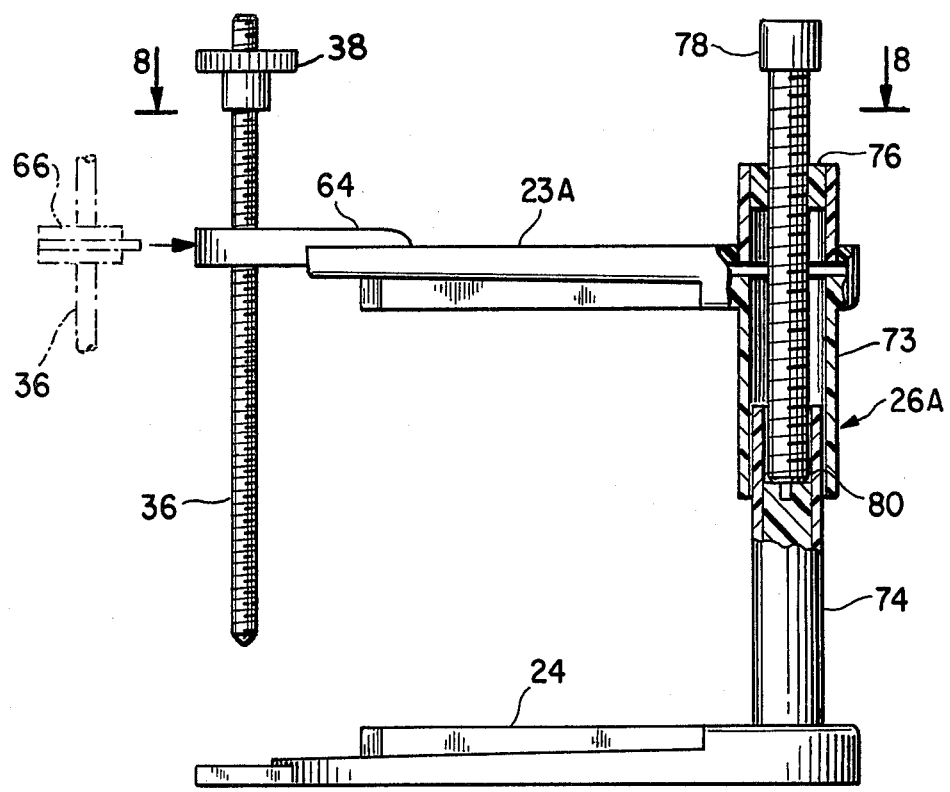
FIG. 7 is a side view of the frame of an articulator of an alternative embodiment of the invention, a portion of a leg of the frame being sectioned to shown an adjustment screw therein.

Referring now to FIG. 7, there is seen an alternative embodiment of the frame of a dental articulator similar to the articulator 20 of FIG. 1, the articulator of FIG. 7, identified by the legend 20A, has an upper platform 23A including a wing 64 which houses a retainer plate 66 through which the spacer 36 is threaded. The retainer plate 66 is removably secured in the front portion of the wing 64 so as to facilitate removal of the spacer 36 when it is desired to insert or remove the trays 29-30 of FIG. 1. By use of the plate 66, the spacer 36 need no longer be unthreaded from the wing of the upper platform as was taught with reference to the embodiment of FIG. 1 in order to provide access to the trays 29-30, access to the trays 29-30 is had simply by sliding out the plate 66 with the spacer 36 therein.

Figure 8:
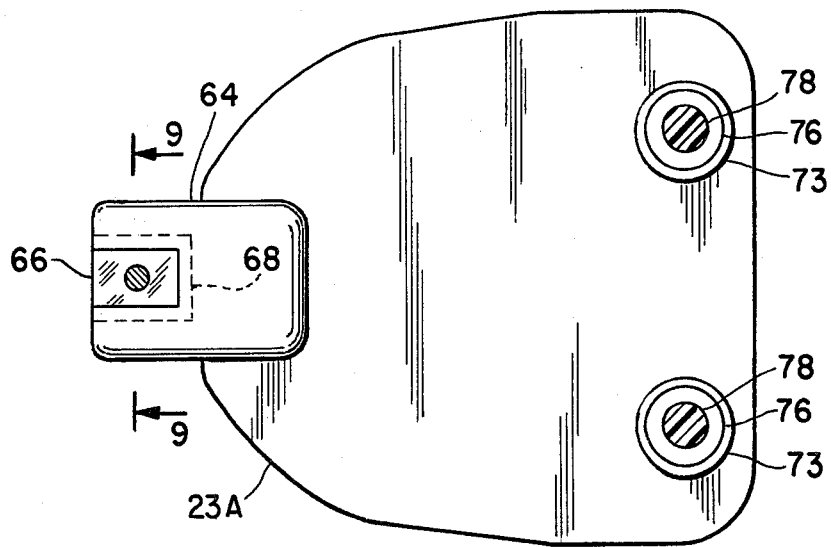
FIG. 8 is a plan view of an upper platform of the articulator frame of FIG. 7 taken along the line 8—8 in FIG. 7.
Figure 9:
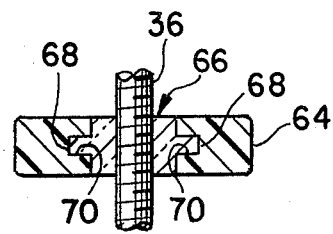
FIG. 9 is a sectional view of a removable plate supporting a spacer in FIGS. 7-8.

With reference also to FIGS. 8 and 9, the plate 66 is seen to have flanges 68 which slidably nest in slot 70. Removal of the plate 66 with the spacer 36 therein is shown in phantom in FIG. 7. The mating surfaces of the platforms 23A and 24, for mating the platforms 23A-24 with the respective trays 29-30, are the same as those disclosed previously with reference to the embodiment of FIG. 1.

In lieu of the clamp 60 of FIG. 1, the embodiments of FIGS. 7-9 show an alternative structure for the leg 26 of FIG. 1, the alternative structure being shown in a leg idenfied by the legend 26A in FIG. 7-8. The leg 26A comprises an upper leg 73 and a lower leg 74. The upper leg 73 includes a threaded cap 76 through which is threaded by a screw 78. The lower leg 74 includes a recess 80 which houses the lower end of the screw 78. By turning the screw 78, the cap 76 is raised up from, or lowered towards, the recess 80 depending on the direction of rotation of the screw 78. Thereby, the upper leg 73 is raised or lowered relative to the lower leg 74 with a corresponding displacement between the platforms 23A-24. The embodiment of the articulator frame depicted in FIG. 7 provides for a three-point suspension of the upper platform 23A relative to the lower platform 24, with each point of the suspension incorporating a threaded member, the threaded spacer 36 and the two screws 78, whereby the spacing between the platforms 23A-24 is readily selected while the orientation between the two platforms is maintained in a parallel disposition.

Figure 10:
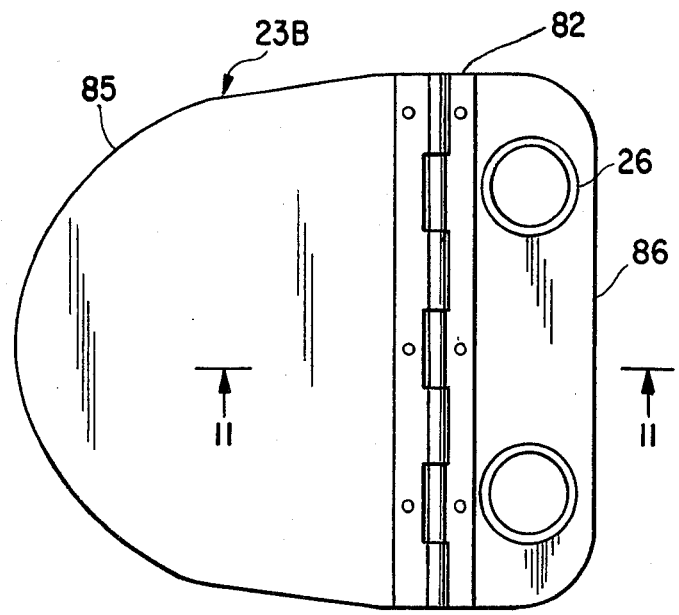
FIG. 10 shows yet a further structural feature in the form of a hinge in the upper platform of the articulator of FIG. 1.
Figure 11:
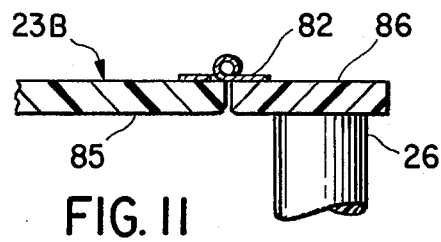
FIG. 11 shows a side view of the hinge of FIG. 10.

Referring now to FIGS. 10-11, there is seen a further structural feature which may be incorporated into the upper platform 23 of FIG. 1 or the upper platform 23A of FIG. 7, the feature being a hinge 82 to provide a hinged upper platform 23B. The hinge 82 joins together a swing portion 85 and a fixed portion 86 of the upper platform 23B. The hinge 82 permits the upper tray 29 of FIG. 1 to be swung upwards and away from the lower tray 30 to facilitate utilization of the lower dental casting 34 in the lower tray 30 without having to remove the spacer 36 of FIGS. 1, 2 and 7. The hinge 82 extends transversely of the upper platform 23B in front of the legs 26.

Figure 12:
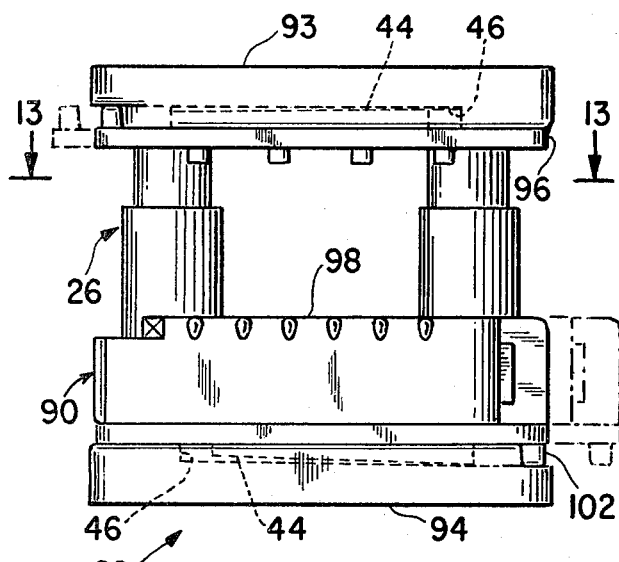
FIG. 12 shows a front view of a further embodiment of the articulator useful in supporting a quadrant casting.
Figure 13:
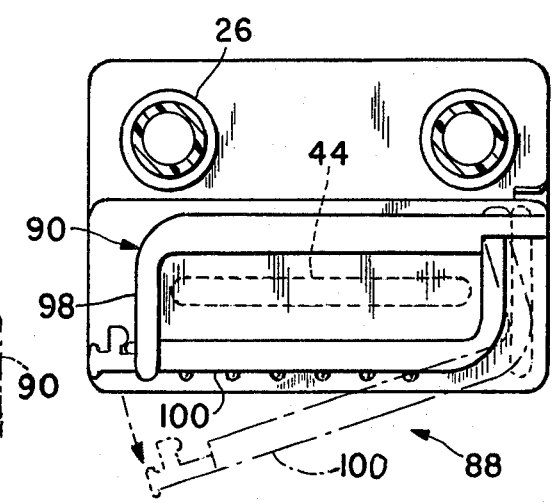
FIG. 13 is a plan view of a portion of the articulator of FIG. 12 taken along the line 13—13 in FIG. 12.

Referring now to FIGS. 12 and 13, there is seen an embodiment of the dental articulator of the invention which is useful for the placement of dental castings of a quadrant of the human mouth. Since the quadrant casting is substantially smaller than the full casting shown in FIGS. 1-2, a two-point suspension utilizing either the leg 26 of FIGS. 1-2 or the legs 26A of FIG. 7 may be utilized. Also, the spacer 36 of FIGS. 1, 2 and 7 may be deleted. The quadrant articulator 88 of FIGS. 12-13 employs a tray 90 which is substantially smaller than either of the trays 29-30 of FIGS. 1-2, the tray 90 having a generally rectangular shape. The tray 90, may be employed either on the upper platform 93 or the lower platform 94. Typically two of the trays 90 would be deployed simultaneously on the upper and lower platforms 93-94. By way of example, only one tray 90 is shown in each of the FIGS. 12-13, that tray being deployed on the lower platform 94 while a modified tray 96 is shown deployed on the upper platform 93. Both the trays 90 and 96 are adapted for receiving dental castings. In the case of the tray 96, the dental casting (not shown in FIG. 12-13, but being similar to those shown in FIGS. 1-2) is secured to the tray 96 by adhesion. With respect to the tray 90, the dental casting is enclosed within a fence 98 having a gate 100 which swings open. The gate 100, in its open position, is shown in phantom in FIG. 13.

Since the tray 90 and the tray 96 are substantially smaller than the trays 29-30, the danger of jamming due to the presence of particulate matter is substantially reduced. Accordingly, the legs 48 of FIGS. 3 have been deleted in FIGS. 12-13. However, the trays 90-96 each employ the key 44 within keyways 46 of the platform 93-94 as has been described previously with reference to the articulator 20 of FIGS. 1-6. Each of the trays 90 and 96 is advantageously provided with a stop 102 which contacts the end of the keyway 46 upon insertion of the tray 90 (or the tray 96) within one of the platforms 93-94. The keyway 46 is oriented sidewise, parallel to a plane containing the centerline of the legs 26.

In order to permit the emplacement of the tray 90 (and similarly with the tray 96) on either the platform 93 or the platform 94, the keyway 46 on the lower platform 94 opens from the right while the corresponding keyway 46 on the upper platform 93 opens from the left. Thus, the tray 90, upon emplacement on the lower platform 94, is inserted from the right side; and during emplacement of the tray 90 on the upper platform 93, the tray 90 is inserted from the left side. Positions of the trays 90 and 96, at partial insertions, are shown in phantom in FIG. 12. Thus, it is seen that the articulator 88 of FIGS. 12-13 may be advantageously employed for quadrant castings in a manner analogous to that described with reference to the articulator 20 of FIGS. 1-6.

It is to be understood that the above-described embodiments of the invention are illustrative only and that modifications thereof may occur to those skilled in the art. Accordingly, the invention is not to be regarded as limited to the embodiment disclosed herein, but is to be limited only as defined by the appended claims.

What is claimed is:

1. A dental articulator comprising:
   an upper platform and a lower platform;
   means for spacing said upper platform relative to said lower platform including a plurality of legs on which said upper platform can translate relative to said lower platform while maintaining a parallel attitude to said lower platform during a translation of said upper platform relative to said lower platform, and a spacer for holding said upper platform in a selected position relative to said lower platform;
   upper and lower trays releasably secured, respectively, to said upper platform and said lower platform;
   each of said trays including a longitudinally disposed key;
   each of said platforms including a longitudinally disposed keyway for mating with said key;
   each of said keyways has side walls which are resiliently supported to the respective ones of said platforms to permit a yielding in the positioning of a tray relative to a platform to facilitate insertion and removal of a tray relative to its platform; and
   wherein
   each of said trays includes a set of spaced-apart legs, said legs being brought into contact with the corresponding one of said platforms upon insertion of the key of a tray into the keyway of the corresponding platform to stabilize the orientations of said trays relative to said corresponding platforms.

2. An articulator according to claim 1 wherein said upper platform is hinged to permit a pivoting of said upper platform.

3. An articulator according to claim 1 wherein a portion of said spacing means is removably secured to said upper platform by a sliding means.

4. A dental articulator comprising:
an upper platform and a lower platform;
means for spacing said upper platform relative to said lower platform;
upper and lower trays releasably securable, respectively, to said upper platform and said lower platform;
each of said trays including a longitudinally disposed key;
each of said platforms including a longitudinally disposed keyway for mating with said key;
each of said keyways having side walls which are resiliently supported to the respective ones of said platform to permit a yielding in the positioning of a tray relative to a platform to facilitate insertion and removal of a tray relative to its platform; and wherein
the legs of any one of said trays are arranged in a triangular array with two of said legs being located towards the rear of said tray, and a third one of said legs being located at the front of said tray.

5. An articulator according to claim 4 where each of said platforms is provided with a guide for guiding legs of the corresponding tray.

6. An articulator according to claim 5 wherein the outer edges of said guide make contact with the inner edges of the rear legs of a tray.

7. A dental articulator comprising:
a platform;
a casting supporting tray removably securable to said platform, said tray including a longitudinal key inclined relative to a surface of said tray, said platform including a keyway inclined relative to a surface of said platform for mating with said key; and wherein
said platform includes means for resiliently supporting sidewalls of said keyway for yieldably engaging sidewalls of said key.

8. An articulator according to claim 7 wherein said side wall support means includes a tongue enclosing a chamber within said platform.

9. An articulator according to claim 8 wherein said platform includes a guide having a guiding edge disposed between said keyway and a path of travel of said tray.

10. An articulator according to claim 9 wherein said tray includes a leg positioned for sliding along said edge of said guide during insertion and removal of said tray from said platform.

11. An articulator according to claim 10 wherein said tray includes a second leg, each of said legs contacting said platform to stabilize the orientation of said tray relative to said platform.

12. A dental articulator comprising:
a platform;
a casting support tray removably secured to said platform;
a key and keyway having means responsive to a transverse movement of said tray relative to said platform for drawing said tray towards said platform along a direction other than said transverse movement, and for securing said tray to said platform; and
a set of legs disposed between said platform and said tray for orienting said tray relative to said platform upon a drawing of said tray towards said platform.

13. A dental articulator according to claim 12 wherein said legs are attached to said tray, and said platform is provided with a guide having a guiding edge for contacting a leg upon a translation of said tray relative to said platform.

14. A dental articulator comprising:
a platform;
a casting supporting tray removably securable to said platform;
means for drawing said tray towards said platform;
a set of legs disposed between said platform and said tray for orienting said tray relative to said platform upon a drawing of said tray towards said platform; and wherein
said drawing means comprises a key and a keyway mating therewith, an interface between said key and said keyway being inclined relative to an interface between said tray and said platform to draw said tray and said platform together upon a passage of said key along said keyway.

* * * * *